United States Patent
Wheeler et al.

(10) Patent No.: US 6,194,415 B1
(45) Date of Patent: *Feb. 27, 2001

(54) METHOD OF USING (2-IMIDAZOLIN-2-YLAMINO) QUINOXOALINES IN TREATING NEURAL INJURY

(75) Inventors: Larry A. Wheeler, Irvine; Elizabeth Woldemussie, Laguna Niguel; Ronald K. Lai, Irvine, all of CA (US)

(73) Assignee: Allergan Sales, Inc.

( * ) Notice: Subject to any disclaimer, the term of this patent is extended or adjusted under 35 U.S.C. 154(b) by 0 days.

This patent is subject to a terminal disclaimer.

(21) Appl. No.: 09/225,036

(22) Filed: Jan. 4, 1999

Related U.S. Application Data

(63) Continuation-in-part of application No. 08/496,262, filed on Jun. 28, 1995, now Pat. No. 5,856,329.

(51) Int. Cl.[7] ................................................. A61K 31/495

(52) U.S. Cl. ......................... 514/255; 514/912; 514/913

(58) Field of Search .............................. 514/252.01, 912, 514/913

(56) References Cited

U.S. PATENT DOCUMENTS

| | | |
|---|---|---|
| 3,890,319 | 6/1975 | Danielewicz et al. . |
| 4,029,792 | 6/1977 | Danielwicz et al. . |
| 5,180,721 | 1/1993 | Burke . |
| 5,215,991 | 6/1993 | Burke . |

FOREIGN PATENT DOCUMENTS

| | | |
|---|---|---|
| 0 422 878 | 10/1990 | (EP) . |
| 0 426 390 | 10/1990 | (EP) . |
| WO 95/16449 | 6/1995 | (WO) . |
| PCT/US95/13624 | 10/1995 | (WO) . |

OTHER PUBLICATIONS

Sabel et al, Neuropsychobiology 28, pp. 62–65 (1993), "Functional Recovery and Morphological Changes after Injury to the Optic Nerve".

Stys et al, "Compound action potential of nerve recorded by suction electrode: a theoretical and experimental analysis", Brian Research, 546 (1991) pp. 18–32.

Ruben et al, Eye 8, pp. 516–520 (1994), "Electrophysiology and Psychophysics in Ocular Hypertension and Glaucoma: Evidence for Different Pathomechanisms In Early Glaucoma".

Burke et al, "Ocular effects of a relatively selective Alpha–2 agonist (UK–14, 304–18) in cats, rabbits and monkeys", Current Eye Research, vol. 5, No. 9, 1986, pp. 665–676.

Michel et al, "Keeping an eye on the I site: imidazoline–preferring receptors", TiPS–Oct. 1992 [vol. 13], pp. 369–370.

Schumer et al, "The Nerve of Glaucoma", Arch. Ophthalmol. vol. 112, Jan. 1994, pp. 37–44.

Johnson et al, Arch. Ophthalmol., vol. 113(1) pp. 70–76, Jan. 1995, "Short–Wavelength Automated Perimetry in Low–, Medium–, and High–Risk Ocular Hypertensive Eyes".

Pfeiffer et al, "The pattern–electroretinogram in glaucoma and ocular hypertension", German Journal of Ophthalmology 1, pp. 35–40, 1992.

Burk et al, Graefe's Arch. Clin. Exp. Ophthalmol, 230 (6), pp. 552–560, 1992, "Are large optic nerve heads susceptible to glaucomatous damge at normal intraocular pressure?".

Trick, Documenta Ophthalmologica 85: pp. 125–134 (1993), "Visual dysfunction in normotensive glaucoma".

Schmidt et al, Ophthalmologica, 212, pp. 5–10, 1998, "Ocular Pulse Amplitude in Ocular Hypertension and Open–Angle Glaucoma".

Kerr et al, Am. J. Ophthalmol., vol. 126 (1) pp. 42–51, 1998, "A Comparison of Ocular Blood Flow in Untreated Primary Open–angle Glaucoma and Ocular Hypertension".

Cioffi et al, Survey of Ophthalmology, vol. 38, Suppl. pp. S107–S116, May 1994, "Microvasculature of the Anterior Optic Nerve".

Schulzer et al, British Journal Ophthalmology, vol. 74, pp. 916–200, 1990, "Biostatistical evidence for two distinct chronic open angle glaucoma populations".

Lamping et al, Ophthalmology, vol. 93 (1), pp. 91–101, Jan. 1986, "Long–term Evaluation of Initial Filtration Surgery".

(List continued on next page.)

*Primary Examiner*—Zohreh Fay
(74) *Attorney, Agent, or Firm*—Robert J. Baran; Carlos A. Fisher; Martin A. Voet

(57) ABSTRACT

The present invention provides a method of protecting the optic or retinal nerve cells of a mammal comprising administering to said mammal suffering from or at risk of suffering a noxious action on said nerve cells an effective amount of a compound of formula I to inhibit or prevent nerve cell injury or death

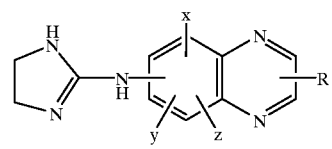

formula I wherein the 2-imidazolin-2-ylamino group is in either the 5- or 6-position of the quinoxaline nucleus; x, y and z are in any of the remaining 5-, 6-, 7- or 8-positions and are selected from hydrogen, halogen, lower alkyl, lower alkoxy or trifluoromethyl; and R is an optional substituent in either the 2- or 3-position of the quinoxaline nucleus and may be hydrogen, lower alkyl or lower alkoxy, or pharmaceutically acceptable salts thereof and mixtures thereof. Such noxious action may result from glaucomatous optic neuropathy, age related macular degeneration or retinitis pigmentosa.

6 Claims, 4 Drawing Sheets

OTHER PUBLICATIONS

Figure 1:
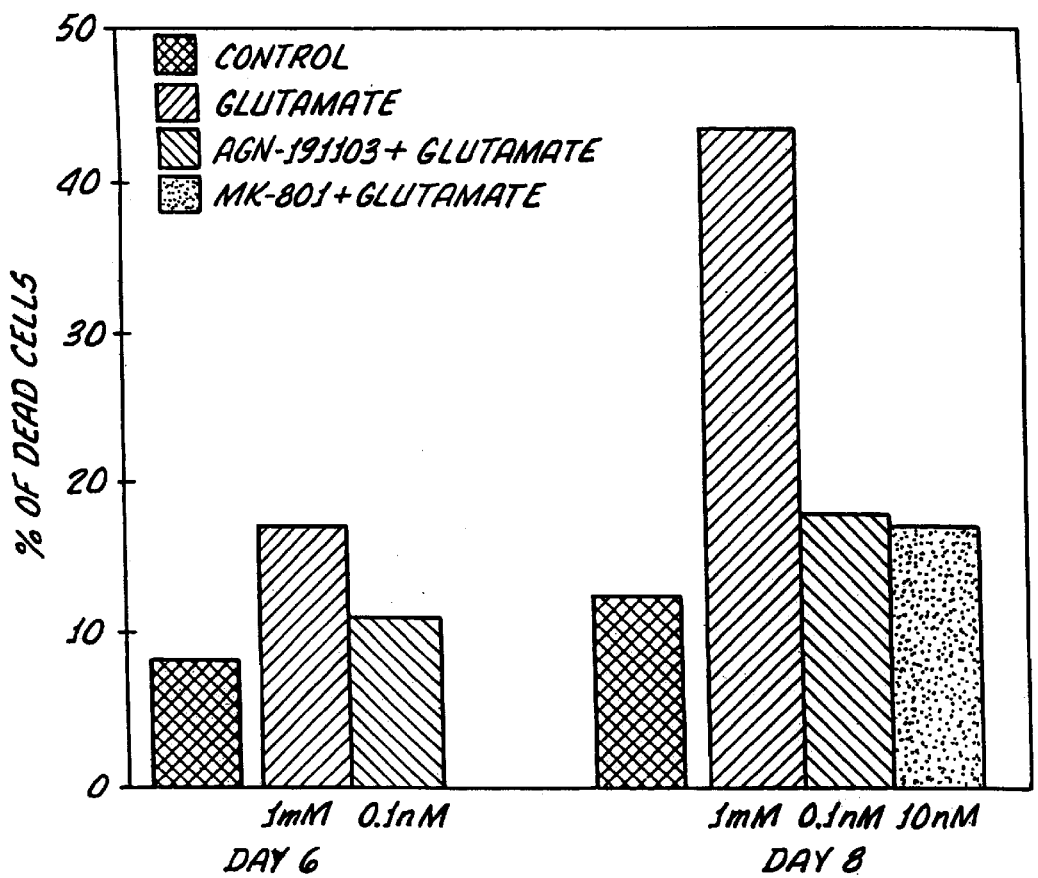

Spaeth, Eur. J. Ophthal. 6 (2), pp. 101–105 (1996), "Proper outcome measurements regarding glaucoma: the inadequacy of using intraocular pressure alone".

Quigly et al, Invest. Ophth. Vis. Sci., 36 pp. 774–786 (1995), "Retinal Ganglion Cell Death in Experimental Glaucoma and After Axotomy Occurs by Apoptosis".

Marsala et al, Journal of Neuroscience Methods 74, pp. 97–106 (1997), "Technique of selective spinal cord cooling in rat: methodology and application".

Lawhead et al, Anesthesiology 77, pp. 983–991 (1992), "α–2A Is the Predominant α–2 Adrenergic Receptor Subtype in Human Spinal Cord".

Marsala et al, J. Neuroscience Methods 62, pp. 43–53 (1995), "The spinal loop dialysis catheter: characterization of use in the unanesthetized rat".

Taira et al, Stroke 27 (10), pp. 1850–1858 (1996), "Effect of Proximal Arterial Perfusion Pressure on Function, Spinal Cord Blood Flow, and Histopathologic Changes After Increasing Intervals of Aortic Occlusion in the Rat".

Marsala et al, Stroke 25 (10), pp. 2038–2046 (1994), "Effect of Graded Hypothermia (27° to 34°C) on Behavioral Function, Histopathology, and Spinal Blood Flow After Spinal Ischemia in Rat".

METHOD OF USING (2-IMIDAZOLIN-2-YLAMINO) QUINOXOALINES IN TREATING NEURAL INJURY

This application is a continuation in part of Ser. No. 08/496,292, filed Jun. 28, 1995, now U.S. Pat. No. 5,856,329.

FIELD OF THE INVENTION

The present invention relates to methods for the protection of nerve cells, including the retina, optic nerve and spinal cord of mammals from noxious provocations including damage from compressive or mechanical effects or trauma or stress factors, including but not limited to impaired blood flow to the nerves, and with respect to the retina and optic nerve, glaucoma, retinitis pigmentosa, and age-related macular degeneration.

BACKGROUND OF THE INVENTION

Glaucoma is a disease of the eye characterized at least initially by increased intraocular pressure. On the basis of its etiology, glaucoma has been classified as primary or secondary. Primary glaucoma is an independent syndrome in adults and may be classified as either chronic open-angle or chronic angle-closure. Primary open angle glaucoma is the most commonly occurring form of glaucoma where there is no other attributable underlying cause. Angle-closure glaucoma usually afflicts those persons having "shallow" angles in the anterior chamber and results from the sides (or angles) of the chamber coming together and blocking aqueous outflow through the trabecular meshwork. Secondary glaucoma, as the name suggests, results from pre-existing ocular diseases such as uveitis, intraocular tumor or enlarged cataract.

The underlying causes of primary glaucoma are not yet well known. Increased intraocular pressure can be a result of obstruction of aqueous humor outflow. In chronic open-angle glaucoma, the anterior chamber and its anatomic structures appear normal, but drainage of the aqueous humor is impeded. In acute and chronic angle-closure glaucoma, the anterior chamber is shallow, the filtration angle is narrowed and the iris may obstruct the trabecular meshwork at the entrance to the canal of Schlemm. Dilation of the pupil may push the root of the iris forward against the angle or may produce pupillary block and thus precipitate an acute attack of elevated intraocular pressure. Eyes with narrow anterior chamber angles are predisposed to acute angle-closure glaucoma attacks of varying degrees of severity.

Secondary glaucoma is caused by any interference with the flow of aqueous humor from the posterior chamber into the anterior chamber and, subsequently, into the canal of Schlemm. Inflammatory disease of the anterior segment may prevent aqueous escape by causing complete posterior synechia in iris bombé, and may plug the drainage channel with exudates. Other common causes are intraocular tumors, enlarged cataracts, ventral retinal vein occlusion, trauma to the eye, operative procedures and intraocular hemorrhage.

Considering all types together, glaucoma occurs in about 2% of all persons over the age of 40 and may be asymptomatic for years before progressing to rapid loss of vision. It is not clear whether glaucomatous nerve damage is the end result of one pathological process or whether there are several mechanisms by which the final disease is manifest.

There is growing evidence that more than one patho-mechanism may be involved early in the glaucomatous process. See for example: Ruben, S. T., Hitchings, et al., *Eye* 8 (5) pp 516–20 (1994). Among these risk factors are elevated intraocular pressure, family history of glaucoma, age and the vertical cup-to-disk ratio of the internal structures in the posterior chamber of the eye. One study found that in hypertensive eyes without visual field loss, the most important factors in predicting the likelihood of glaucoma-induced loss were the cup-to-disk ratio and age. Johnson, C. A., Brandt, J. D., et al., *Arch. Ophthalmol.* 113 (1) pp. 70–76 (1995) These studies implicitly assume that there are persons who have elevated intraocular pressure (ocular hypertension) without nerve damage to the optic disk or the retina. See also: Pfeiffer N., Bach, M. *Ger. J. Ophthalmol.* 1 (1) pp.35–40 (1992). Glaucomatous field damage is also known to occur in the eyes of individuals with normotensive intraocular pressure. One theory is that the size of the optic disk determines the susceptibility of the nerve head to glaucomatous visual field damage at statistically normal intraocular pressure. Burk, R. O., Rohrschneider, K., Noack, H., et al. *Graefes Arch. Clin. Exp. Ophthalmol.* 230 (6) pp. 552–60 (1992). Another explains visual field damage at normotensive pressure as occurring by a different, as yet unidentified, pathologic mechanism. Trick, G. L., *Doc. Ophthalmol.* 85 (2), pp. 125–33 (1993). Regardless of the theory, glaucomatous visual field damage at statistically normal intraocular pressure is a clinically recognized condition.

Elevated intraocular pressure, while being generally acknowledged as a risk factor for the possible onset of glaucoma, is not a necessary condition for glaucomatous field damage. Nerve cell damage can occur with or without elevated intraocular pressure and nerve cell damage does not necessarily occur in individuals who experience elevated intraocular pressure. Two studies have suggested that increased choroidal perfusion (circulation) may help to prevent glaucomatous optic nerve damage in patients with ocular hypertension. Schmidt, K. G., von Ruckmann, A., et al., *Ophthalmologica,* 212 (1) pp. 5–10 (1998) and Kerr J; Nelson P; O'Brien C, *Am J Ophthalmol.,* 126 (1) pp. 42–51 (1998). Thus, modernly it appears that glaucoma is characterized as a complex syndrome that manifests itself as optic nerve damage with or without elevated intraocular pressure. It further appears that each symptom, either elevated intraocular pressure or glaucomatous damage to nerve cells, can occur independently of the other. The present invention provides methods to protect retinal ganglion cells and the optic nerve that are damaged or lost despite a therapeutic lowering of intraocular pressure to within normal levels; to protect such cells from damage in the case of so-called normotensive glaucoma; and to protect such cells in glaucomatous eyes that do not respond adequately to treatment modalities intended to lower intraocular pressure.

In cases where surgery is not indicated, topical beta-adrenoceptor antagonists have been the drugs of choice for treating glaucoma. However, alpha adrenergic agonists have more recently been approved for use in the treatment of elevated intraocular pressure and are probably becoming mainstays in the treatment of this disease. Among this class of drugs are various quinoxaline derivatives having alpha$_2$ agonist activity which were originally suggested as therapeutic agents by Danielewicz, et al. in U.S. Pat. Nos. 3,890,319 and 4,029,792. These patents disclose compounds as regulators of the cardiovascular system which have the following formula:

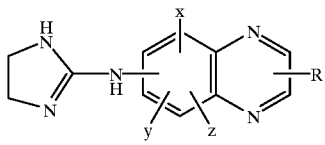

formula I where the 2-imidazolin-2-ylamino group may be in any of the 5-, 6-, 7- or 8-position of the quinoxaline nucleus; x, y and z may be in any of the remaining 5-, 6-, 7- or 8-positions and may be selected from hydrogen, halogen, lower alkyl, lower alkoxy or trifluoromethyl; and R is an optional substituent in either the 2- or 3-position of the quinoxaline nucleus and may be hydrogen, lower alkyl or lower alkoxy. The presently useful compounds may be prepared in accordance with the procedures outlined by Danielewicz, et al. The contents of both U.S. Pat. Nos. 3,890,319 and 4,029,792 are hereby incorporated by reference in their entirety.

In Ocular Effects of a Relatively Selective Alpha-2 Agonist (UK-14,304-18) in Cats, Rabbits and Monkeys [J. A. Burke, et al., *Current Eye Rsrch.*, 5, (9), pp. 665–676 (1986)] the quinoxaline derivative shown below and having the generic name brimonidine was shown to be effective in reducing intraocular pressure in rabbits, cats and monkeys. Compounds in this study were administered topically to the corneas of the study animals.

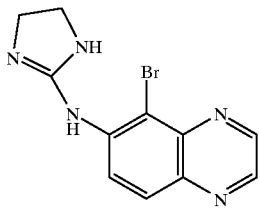

It has long been known that one of the sequelae of glaucoma is damage to the optic nerve head. The optic nerve head or optic disk is where, along with the retinal vasculature, the axons of the retinal ganglion cell (RGC) bodies that are distributed along the upper layer of the retina converge and are bundled together to transmit signals to the lateral geniculate nucleus. (See diagram of FIG. 6) Damage to the optic nerve head, clinically referred to as cupping, is observable as areas of depression in the nerve fibers of the optic disk. Cupping is the result of death of optic nerve fibers and alterations in the lamina cribosa, an extracellular matrix that provides structural support. Loss of peripheral vision is a consequence of RGC demise and usually goes undetected until more advanced stages of the disease wherein up to fifty percent of the retinal ganglion cells may already be damaged or lost. Left untreated glaucoma can progress from dimming of vision or loss of acuity to total blindness.

Unfortunately despite long-term lowering intraocular pressure to statistically normal levels by administration of drugs or by surgery to facilitate outflow of the aqueous humor, damage to the nerves in glaucomatous conditions still persists in a significant number of patients. This apparent contradiction is addressed by Cioffi and Van Buskirk [*Surv. of Ophthalmol.*, 38, Suppl. p. S107–16, discussion S116–17, May 1994] in the article, Microvasculature of the Anterior Optic Nerve. They state:

The traditional definition of glaucoma as a disorder of increased intraocular pressure (IOP) oversimplifies the clinical situation. Some glaucoma patients never have higher than normal IOP and others continue to develop optic nerve damage despite maximal lowering of IOP.

The fact that the nerve damage associated with glaucoma may progress even after significant reduction of intraocular pressure has led many to suggest that pressure-independent causes contribute in many cases. See for example: Schulzer M, et al., "Biostatistical evidence for two distinct chronic open-angle glaucoma populations" Br. J. Ophthal. pp 74916–74200 (1990); Lamping K A, et al., "Long-term evaluation of initial filtration surgery" Ophthalmolgy 93 (1) PP.91–101 (1986); Migdal, 1994; Spaeth G L "Proper outcome measurements reagrding glaucoma: the inadequacy of using intraocular pressure alone." Eur. J. Ophthal. 6 (2) pp 101–105 (1996). These causes have been suggested to include: (1) induction of apoptosis (programmed cell death) of retinal ganglion cells which is a genetically controlled process whereby unneeded or damaged cells die without eliciting an inflammatory response (see for example: Quigely H A, et al. Invest. Ophth. Vis. Sci., 36 pp.774–786 (1995) "Retinal Ganglion Cell Death in Experimental Glaucoma and after Axotomy Occurs by Apoptosis") and (2) further neuronal degeneration affecting cells (which were not injured by the primary insult) after death or injury of incipiently injured nerve cells. The damage to nerve cells secondary to the primary injury result from overaccumulation of excitatory neurotransmitters released and other noxious environmental conditions created by the death and degeneration of neighboring RGCs. More minor contributors or less understood components in glaucomatous optic neuropathy are: genetic determinants contributing to irregularities in the metabolism of the extracellular matrix and hence susceptibility of the RGCs to damage; vascular compromise which promotes ischemia whether or not related to elevated IOP; and metabolic disorders. Another advantage of the present invention is that it provides a more direct and broader level of protection to nerves because the compounds of the present invention afford protection at the locus of neural damage from both primary and secondary causes.

Retinitis pigmentosa is the term for a group of inherited diseases that affect the retina, the delicate nerve tissue composed of several cell layers that line the inside of the back of the eye and contain photoreceptor cells. These diseases are characterized by a gradual breakdown and degeneration of the photoreceptor cells, the so-called rods and cones, which results in a progressive loss of vision. It is estimated that retinitis pigmentosa affects 100,000 individuals in the United States. The rods are concentrated outside the center of the retina, known as the macula, and are required for peripheral vision and for night vision. The cones are concentrated in the macula and are responsible for central and color vision. Together, rods and cones are the cells responsible for converting light into electrical impulses that transfer messages to the retinal ganglion cells which in turn transmit the impulses through the lateral geniculate nucleus into that area of the brain where sight is perceived. RP therefore affects a different retinal cell type of the than those affected by glaucoma. Most common in all types of retinitis pigmentosa is the gradual breakdown and degeneration of the rods and cones. Depending on which type of cell is predominantly affected, the symptoms vary, and include night blindness, lost peripheral vision (also referred to as tunnel vision), and loss of the ability to discriminate color before peripheral vision is diminished.

Symptoms of retinitis pigmentosa are most often recognized in adolescents and young adults, with progression of the disease usually continuing throughout the individual's life. The rate of progression and degree of visual loss are variable. As yet, there is no known cure for retinitis pigmentosa.

While not a cure, certain doses of vitamin A have been found to slightly slow the progression of retinitis pigmentosa in some individuals. Researchers have found some of the genes that cause retinitis pigmentosa. It is now possible, in some families with X-linked retinitis pigmentosa or autosomal dominant retinitis pigmentosa, to perform a test on genetic material from blood and other cells to determine if members of an affected family have one of several retinitis pigmentosa genes, and therefore to begin therapy before the damaging effects of the disease become manifest. It is an object of the present invention to protect the photoreceptor cells, the rods and cones by the compounds and methods described herein, particularly in regard to the studies of protection of the photoreceptor cells to light induced damaged by neuroprotective compounds.

Age-related macular degeneration (ARMD) is degenerative condition of the macula or central retina. It is the most common cause of vision loss in the Western world in the over 50 age group. It most commonly affects those of northern European descent and is uncommon in African-Americans and Hispanics. Its prevalence increases with age and affects 15% of the population by age 55 and over 30% are affected by age 75. Macular degeneration can cause loss of central vision and make reading or driving impossible, but unlike glaucoma, macular degeneration does not cause complete blindness since peripheral vision is not affected. Macular degeneration is usually obvious during ophthalmologic examination.

Macular degeneration is classified as either dry (non-neovascular) or wet (neovascular). In its exudative, or "wet," form, a layer of the retina becomes elevated with fluid, causing retinal detachment and wavy vision distortions. Abnormal blood vessels may also grow into, or under, the retina, creating a neovascular membrane that can leak, further obscuring vision. In advanced cases, scar tissue forms, causing irreversible scotomas, or blind spots. Dry macular degeneration, although more common, typically results in less severe, more gradual loss of vision as one or more layers of the retina degenerates and atrophies. Yellow deposits, called "drusen," or clumps of pigment may appear.

In both forms, the area of the retina affected is the macula (3)—the most sensitive area of the retina. For this reason, people with macular degeneration lose central vision and the ability to see fine detail, while their peripheral vision remains unchanged.

In the case of age related macular degeneration, treatments have been proposed and studied but have found limited success in clinical application. Laser photocoagulation is effective in sealing leaking or bleeding vessels. Unfortunately, it usually does not restore lost vision but only slows or prevents further loss. Conventional laser treatment for exudative macular degeneration generally is effective for a limited amount of time because the abnormal blood vessels tend to grow back.

A newer, investigational approach, photodynamic therapy, has shown some promising results in the treatment of wet (neovascular) ARMD. An injection of a photosensitive dye is given systemically to a patient, which is taken up only in abnormal tissues such as the abnormal vessels present in wet ARMD "A "cold" laser is directed into the eye which activates the dye taken up in the cell walls of the abnormal vessels, thus forming oxidative compounds that lead to clot formation in the neovascular tissues. Fluid leakage is thus halted and as the remaining fluid is reabsorbed, vision improves. Unfortunately, the body also absorbs the clot in 4–12 weeks, so the procedure must be repeated, and, additionally, the laser treatment can cause photic damage to the retina. Another aspect of the present invention is that the compounds of the invention may be administered to protect the retina from damage by the laser light used as a part of this ARMD therapy.

An invasive surgical technique also has been developed that uses specialized forceps to enter into the eye and pull out the neovascular membrane. Unfortunately the neovascularization often grows back.

The cells that nurture the retina, the cells of the retinal pigment epithelium, as well as photoreceptor tissues, have been harvested from human fetal tissues grown in the laboratory and then transplanted. In studies of rats with inherited retinal disease, human fetal retinal pigment epithelium was surgically introduced into the eyes where it functioned normally and restored vision. Unfortunately, transplants in human studies, while initially successful, have failed within three months owing to rejection.

Thus it is evident that there is an unmet need for agents that have neuroprotective effects that can stop or retard the progressive damage resulting from one or more noxious provocations to nerve cells.

SUMMARY OF THE INVENTION

A new method of protecting the nerve cells of the eye and the spine of a mammal from noxious provocations has been discovered. This method comprises administering to the mammal either systemically, topically, intrathecally, epidurally or by intrabulbar injection an effective amount of one or more of certain aryl-imino-2-imidazolidines (as defined herein), salts thereof and mixtures thereof.

For for treatment of glaucomatous retin in humans suffering from that condition, the active compounds (or mixtures or salts thereof) are administered in accordance with the present invention to the eye admixed with an ophthalmically acceptable carrier. Any suitable, e.g., conventional, ophthalmically acceptable carrier may be employed. A carrier is ophthalmically acceptable if it has substantially no long term or permanent detrimental effect on the eye to which it is administered. Examples of ophthalmically acceptable carriers include water (distilled or deionized water) saline and other aqueous media. In accordance with the invention, the active compounds are preferably soluble in the carrier which is employed for their administration, so that the active compounds are administered to the eye in the form of a solution. Alternatively, a suspension of the active compound or compounds (or salts thereof) in a suitable carrier may also be employed.

In accordance with the invention the active compounds (or mixtures or salts thereof) are administered in an ophthalmically acceptable carrier in sufficient concentration so as to deliver an effective amount of the active compound or compounds to the eye. Preferably, the ophthalmic, therapeutic solutions contain one or more of the active compounds in a concentration range of approximately 0.0001% to approximately 10% (weight by volume) and more preferably approximately 0.0005% to approximately 0.5% (weight by volume).

Any method of administering drugs directly to a mammalian eye may be employed to administer, in accordance with the present invention, the active compound or compounds to the eye to be treated. By the term "administering directly" is meant to exclude those general systemic drug administration modes, e.g., injection directly into the patient's blood vessels, oral administration and the like, which result in the compound or compounds being systemically available. The primary effect on the mammal resulting from the direct administering of the active compound or compounds to the mammal's eye is preferably a reduction in intraocular pressure. More preferably, the active useful compound or compounds are applied topically to the eye or are injected directly into the eye. Particularly useful results are obtained when the compound or compounds are applied topically to the eye in an ophthalmic solution (ocular drops).

Topical ophthalmic preparations, for example ocular drops, gels or creams, are preferred because of ease of application, ease of dose delivery, and fewer systemic side effects, such as cardiovascular hypotension. An exemplary topical ophthalmic formulation is shown below in Table 1. The abbreviation q.s. means a quantity sufficient to effect the result or to make volume.

TABLE I

| Ingredient | Amount(% W/V) |
|---|---|
| Active Compound in accordance with the invention, | about 0.0001 to about 1 |
| Preservative | 0–0.10 |
| Vehicle | 0–40 |
| Tonicity Adjustor | 1–10 |
| Buffer | 0.01–10 |
| PH Adjustor | q.s. pH 4.5–7.5 |
| Antioxidant | as needed |
| Purified Water | as needed to make 100% |

Various preservatives may be used in the ophthalmic preparation described in Table I above. Preferred preservatives include, but are not limited to, benzalkonium chloride, chlorobutanol, thimerosal, phenylmercuric acetate, and phenylmercuric nitrate. Likewise, various preferred vehicles may be used in such ophthalmic preparation. These vehicles include, but are not limited to, polyvinyl alcohol, povidone, hydroxypropyl methyl cellulose, poloxamers, carboxymethyl cellulose, hydroxyethyl cellulose, and purified water.

Tonicity adjustors may be added as needed or convenient. They include, but are not limited to, salts, particularly sodium chloride, potassium chloride, mannitol, and glycerin, or any other suitable ophthalmically acceptable tonicity adjustor.

Various buffers and means for adjusting pH may be used so long as the resulting preparation is ophthalmically acceptable. Accordingly, buffers include but are not limited to, acetate buffers, citrate buffers, phosphate buffers, and borate buffers. Acids or bases may be used to adjust the pH of these formulations as needed.

In a similar vein, ophthalmically acceptable antioxidants include, but are not limited to, sodium metabisulfite, sodium thiosulfate, acetylcysteine, butylated hydroxyanisole, and butylated hydroxytoluene. The ophthalmic solution (ocular drops) may be administered to the mammalian eye as often as necessary to obtain the desired concentration intravitreally that affords neuroprotection. For acute neuroprotective effect such as photoprotection in the above described laser treatment for ARMD, the protective agent would be administered in advance of the treatment to provide optimal protection during the laser procedure. For chronic treatments such as in protection of the retinal ganglion cells against damage from the neuropathic effects of for example glaucoma or "dry" ARMD, the drug would be administered as frequently as necessary to maintain desired intravitreal concentration or range of concentrations at all times. In other words, the ophthalmic solution (or other formulation) which contains the α2-adrenergic agent as the active ingredient, is administered to the mammalian eye as often as necessary to maintain the beneficial neuroprotective effect of the active ingredient in the eye. Those skilled in the art will recognize that the frequency of administration depends on the precise nature of the active ingredient and its concentration in the ophthalmic formulation. Within these guidelines it is contemplated that the ophthalmic formulation of the present invention will be administered to the mammalian eye approximately once or twice daily.

Treatment of ARMD using the compounds of the present invention takes a different therapeutic approach than the treatment modalities discussed above which concentrate on treating the vascularization. Treatment with α-adrenergic agonists protects the retinal cells of the macula from damage caused by the noxious provocations of the degenerative process or from damage of laser light used in the treatment. These noxious occurrences include, but are not limited to: laser light damage from the laser procedure without or without photoreactive dye, and atrophy associated with the dry form of ARMD. Thus the α2-adrenergic agonists of the present invention may be administered alone or in conjunction with any of the foregoing described therapies.

This new method is particularly effective when administered as a prophylactic treatment, i.e. before damage to the nerve has taken place, or before long-term progression of the disease state, such as glaucoma, retinitis pigmentosa or ARMD, has taken place. Without wishing to be held to a particular theory regarding the role that the compounds of the present invention play in neuroprotection, applicants hypothesize that the compounds and methods described cause an upregulation of bFGF (a neuronal cell survival factor) expression via $\alpha_2$ stimulation and that this endogenous release may provide neuroprotection by signaling the cells to survive notwithstanding the apoptotic (programmed cell death) signals the cells receive from the noxious provocation. With increased endogenous concentrations of the bFGF in response to the α2 agonism, the balance of cell survival and cell death signals may be shifted towards the promotion of cell survival. Further, it has been found that certain factors of the bcl-2 family are also produced as measured by the increased expression of mRNA encoding their production; these factors labeled bcl-2 and bcl-$x_L$ also suppress the apoptotic program. These factors can counterbalance the presence or induction of bcl-2 apoptosis factors such as bad and bax which may be produced as a result of noxious provocations to the nerve cells. Thus it is further contemplated that the compounds of the present invention which provide cell survival signals to the nerve can advantageously be used in combination with compounds that inhibit cell death. Such cell death inhibiting compounds include NMDA antagonists, especially memantine, which block excitotoxic effects of excess glutamate; nitric oxide synthetase inhibitors; free-radical scavengers and calcium channel blockers.

DETAILED DESCRIPTION OF THE INVENTION

The drawings will first be briefly described.

DRAWINGS

FIG. 1 is a bar graph showing the percentage of cells killed by treatment with glutamate plotted by number of days since glutamate treatment. A control which was not treated with glutamate has been included to determine cell death which occurred without any such treatment. Also shown are measurements taken after treatment with both AGN191103 and glutamate, and treatment with MK-801 and glutamate. MK-801 is a well known neuroprotective agent in the art that acts as an NMDA antagonist. The NMDA receptor binds, among other neurotransmitters, glutamate. The numbers beneath the bars for glutamate; AGN191103+glutamate; and MK-801+glutamate show the concentrations of glutamate and drug used in each case. At day 8, AGN 191103 and MK-801 show comparable effects in protecting cells from glutamate induced neurotoxicity. Experimental procedures followed in generating the data for this figure are detailed in Example 1.

Figure 2:
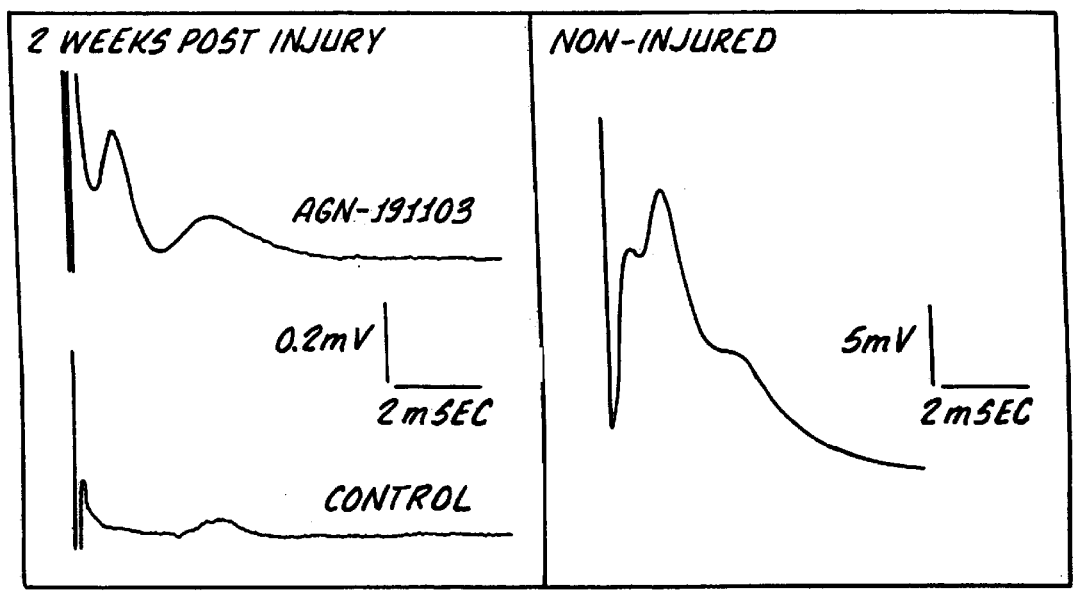

FIG. 2 shows plots of compound action potentials (CAP) measured for optic nerve fibers: in the left-hand frame, measured at 2 weeks post injury (i.e. after nerve crush) for optic nerve treated with AGN 191103 (the upper line) and for an untreated nerve used as a control (lower line); and in the right-hand frame a comparison CAP of non-injured optic nerve. The scales of the plots are given for each of the frames. The post-injury abscissa scale is 25×the scale of the non-injured plot. (Units: millivolts and milliseconds). The value of the compound action potential is calculated as the integral of the area under each curve. The irregularity of the curve is a feature of the dispersion of the compound response; some nerve cells conduct more rapidly than others and so amplitude of the measured voltage varies with time.

Figure 3:
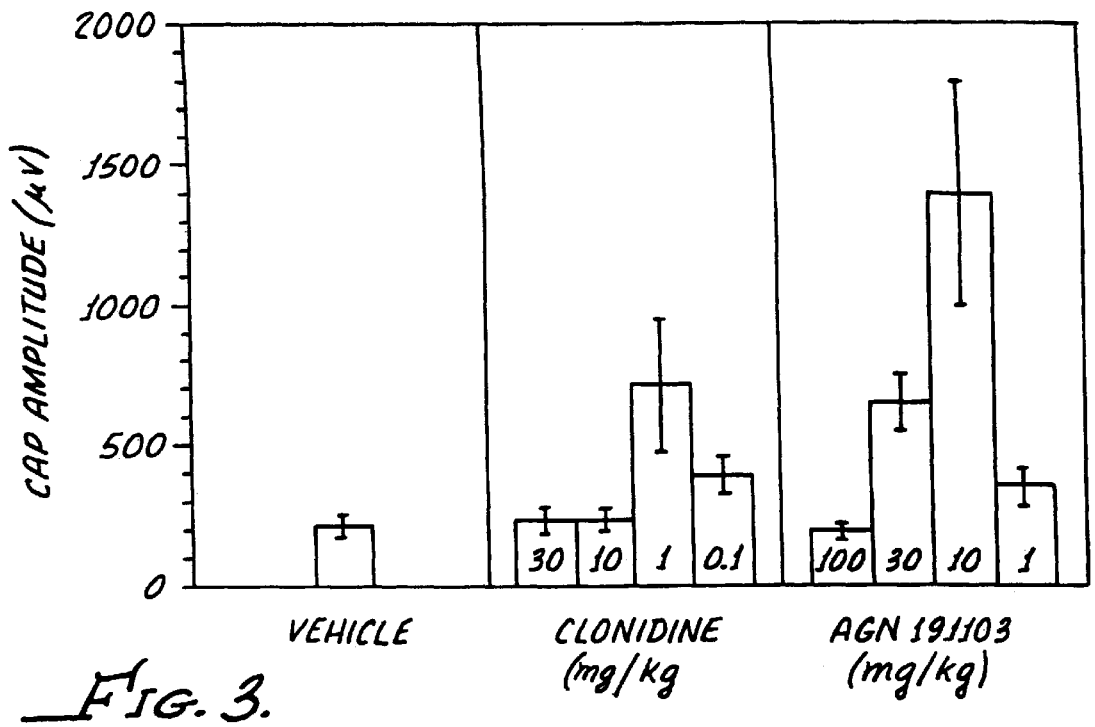

FIG. 3 is a bar graph showing the maximal CAP amplitude in microvolts ($\mu$V) for cells injured by a optic nerve crush in rats and treated with: 1) vehicle alone; 2) clonidine and 3) AGN191103. Each of the drugs was tested at four different concentrations (administered as a multiple of body weight for the test subject) and is represented by a bar on the chart. Clonidine was chosen as a benchmark $\alpha_2$ agonist compound with very well defined pharmacology to compare against the test compound AGN 191103. While clonidine did show some neuroprotective activity over vehicle alone, it showed about half the maximal CAP response of AGN191013.

Figure 4:
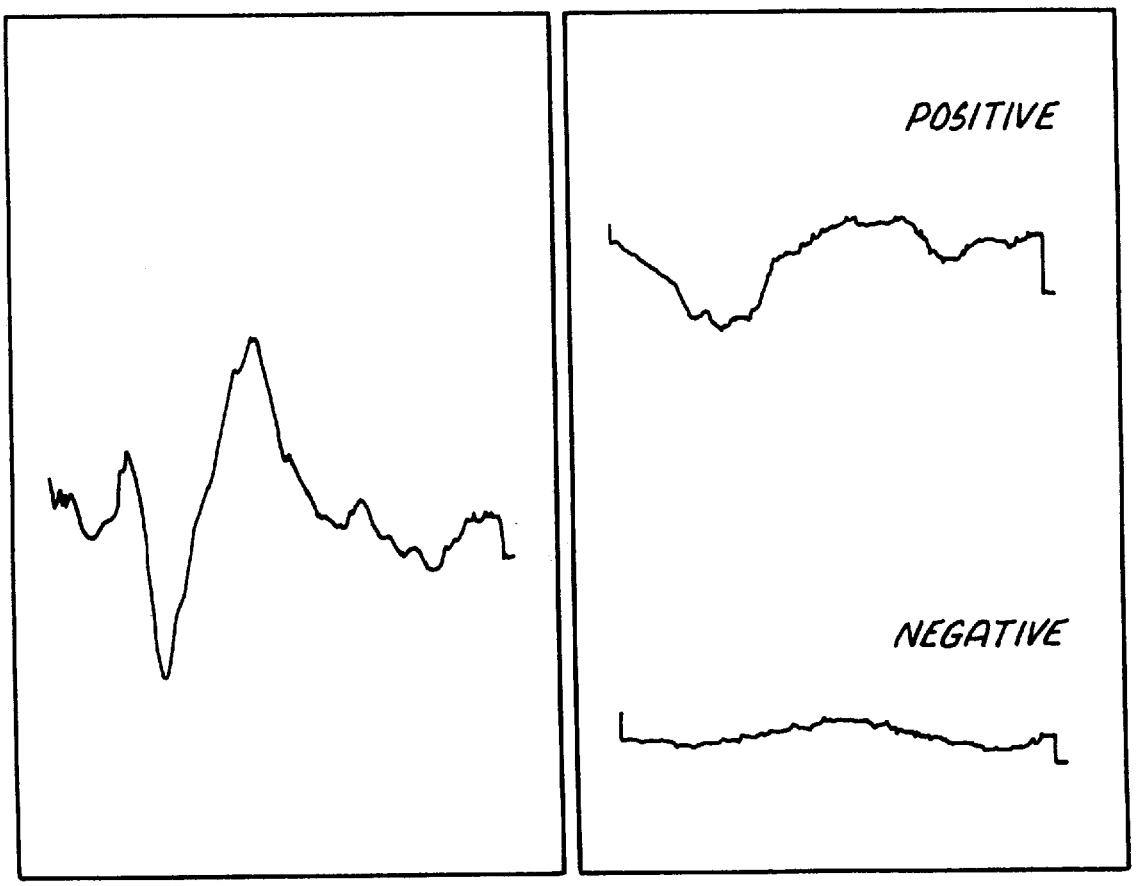

FIG. 4 is a graphic plot of the Visual Evoked Potential Response and shows the electrical potential activity evoked at the surface of the visual cortex (comparable to an electroencephalogram) as a result of visual (light) stimulus. The test is performed in live rats and is a measure of the integrity of the whole visual system from the retina through the optic nerve into the lateral geniculate nucleus and ultimately to the visual cortex located in the back of the brain. The left-hand frame shows the response without nerve crush injury and the right-hand frame shows the responses measured at 2 weeks post-injury for rats treated with AGN191103 above (labeled positive) and control rats below (labeled negative) prior to nerve crush. The scale in $\mu$V vs. milliseconds for both plots is shown below the ordinate axis.

Figure 5:
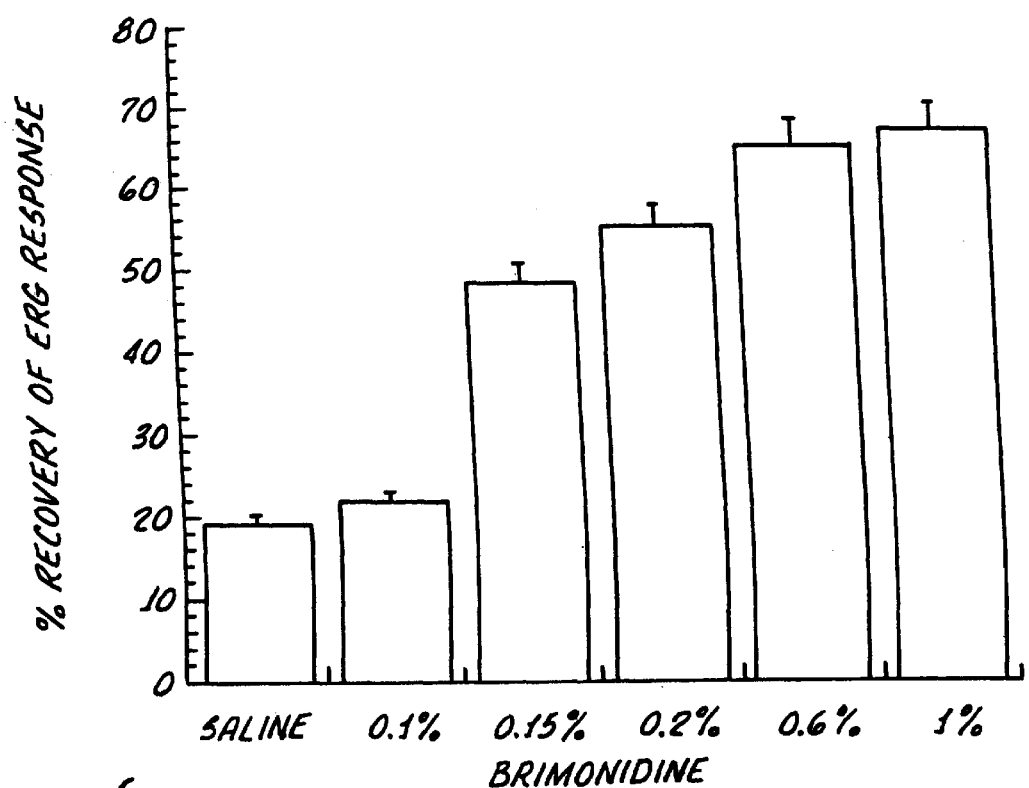

FIG. 5 is a bar graph showing the results of a study to determine the topical efficacy of brimonidine in neuroprotection. The rat acute retinal ischemia model was used to provide the noxious action. Brimonidine was applied topically one hour before ischemic insult, 10 $\mu$l to one eye, 10 $\mu$l saline to the other eye. The ERG (electroretinogram) was measured one week after the insult. The bar graph shows the percent of ERG signal recovery as a function of dosage. The results show that brimonidine provides topical neuroprotection in a dose dependent manner.

Figure 6:
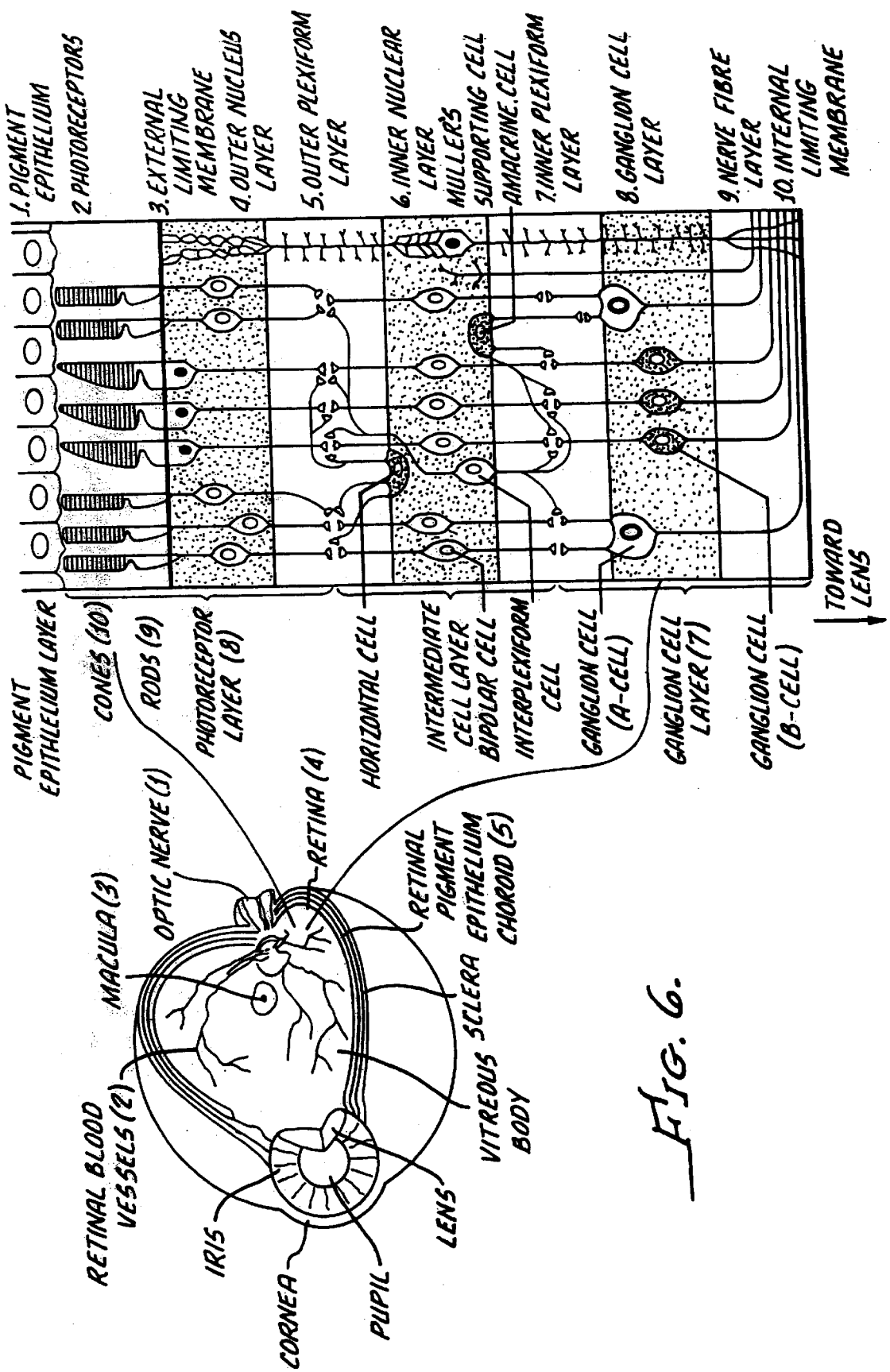

FIG. 6 is a schematic drawing of a cut away section of the eye which shows the anterior and posterior chambers. The former being filled with aqueous humor and separated from the posterior around the lens of the eye. The posterior segment is filled with vitreous humor (6) a clear, viscous liquid that maintains the shape of the eye. At the back of the eye are the retina (4), optic disk (3), and the optic nerve (5). Underlying the retina is the retinal pigment epithelium and choroid (2) which is responsible for maintenance and support of the retinal nerve cells. Further the diagrammatic view of the retina shows the layers of nerve cells and associated helper cells that make up the retina. The first layer of cells contacted by light incoming through the lens is the retinal ganglion cells (7), then at the base of the retina toward the choroid are the photoreceptor cells (8) which are comprised of the rods (9) and cones (10).

For a discussion and bibliography regarding the nerve crush model and its significance in evaluating nerve damage and recovery see: Functional Recovery and Morphological Changes after Injury to the Optic Nerve, Sabel, B. A. and Aschoff, A., *Neuropsychobiology*, 28, pp. 62–65 (1993).

Injury to the mammalian optic nerve, as in any other parts of the mammalian central nervous system (CNS), leads to axonal degeneration followed by a loss of cell bodies, with failure of axonal regrowth from the surviving neurons. Initially, degeneration of the injured nerve is probably attributable to direct neuronal damage. However, the associated physiological and biochemical events occurring in the nerve immediately after injury are probably responsible for the subsequent progressive degeneration, not only of the directly injured axons, but also of those that escaped the primary damage. These secondary effects largely determine the long-term functional outcome.

The immediate injury-induced response strongly influences the subsequent degenerative response. Treatment that reduces or attenuates the immediate response is therefore likely to achieve optimal prevention or delay of the secondary degenerative processes. For monitoring of the immediate response, it is obviously preferable to employ a noninvasive technique. An adaptation of the nicotinamide adenine dinucleotide (NADH) monitoring technique to enable measurement of the earliest post-traumatic events has proved to be a valuable non-invasive approach. Use of the technique allows the immediate effect of the injury to be evaluated in real time and on-line before and after a well-controlled crush injury is inflicted on the adult rat optic nerve in vivo. In this experimental paradigm, measurement of the metabolic activity of the injured optic nerves represent the activity of both injured axons and their associated non neuronal cells, and thus evaluate the potential ability to cope with injurious stresses. The model is also useful for monitoring the activity of various agents that may overcome or mitigate nerve cell damage or death from such stresses.

The earliest injury-induced response is a decrease in the energy state of the nerve, under conditions where ischemic events can be completely ruled out. The reduction in the energy state may be related to: 1) postinjury elevation in free fatty acid levels, which may interfere with mitochondrial function and result in uncoupling of electron transport; and 2) a marked rise in intracellular free $Ca^{2+}$. It is known that axonal injury is generally followed by an increase in extracellular potassium ions, which stimulate the uptake of $Ca^{2+}$ via either voltage sensitive channels (L, T or N type) or receptor-operated $Ca^{2+}$ channels. A marked rise in intracellular free $Ca^{2+}$ can accelerate processes that are inimical to cell survival, including those involving $Ca^2$-dependent enzymes, mainly lipases, proteases and endonucleases, that may cause mitochondrial damage and lead eventually to cell death. The cell, in order to overcome these events, needs more energy to actively restore ionic homeostasis. The combination of increased energy demands and decreased energy conservation resulting from mitochondrial dysfunction at the site of injury may be the major reason for the subsequent irreversible nerve damage and nerve degeneration following injury. Early measurement of metabolic activity could therefore indicate the fate of the axon, its associated glial cells and its non-neuronal cell bodies. It follows from the above that restoration of the mitochondrial activity may be critical in preventing the degenerative process occurring in the nerve after injury.

Since the injury inflicted on the nerve in the nerve crush model is a well-controlled, calibrated and reproducible lesion, it is possible to correlate early post-traumatic metabolic deficits and possible mitigation of these by drug or other treatments with long-term morphological and physiological effects.

From the foregoing figures and discussion it is apparent that neuroprotection is conferred on nerve cells against both glutamate-induced toxicity and physical insult in the nerve crush model.

It has now been discovered that neuroprotection is conferred upon ocular nerve cells by administration of a drug of formula I to the spinal neurons or retina and optic nerve of a mammal within a period prior to, or following an insult to the nerve cells but prior to cell death, formula I

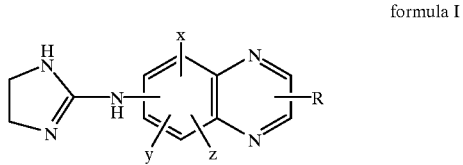

wherein the 2-imidazolin-2-ylamino group may be in either the 5- or 6-position of the quinoxaline nucleus; x, y and z may be in any of the remaining 5-, 6-, 7- or 8-positions and are selected from hydrogen, halogen, lower alkyl, lower alkoxy or trifluoromethyl; and R is an optional substituent in either the 2- or 3-position of the quinoxaline nucleus and may be hydrogen, lower alkyl or lower alkoxy.

DEFINITIONS

The compound identified as AGN 191103 has the chemical structure as shown. It is also known by the chemical nomenclature 6-methyl-(2-imidazolin-2-ylamino) quinoxaline.

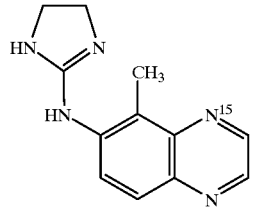

The neuroprotective agent identified as MK-801 is also known by the name dizocilpine and has the following chemical structure:

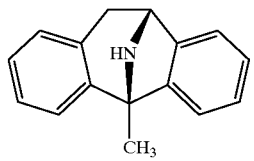

It is additionally identified and described in the 11th edition of the Merck Index at monograph number 3392.

The terms noxious actions or noxious provocations are defined as an occurrence which is harmful or destructive to a nerve cell. It is not limited to events extrinsic to the mammal being treated but includes disease states and physiological occurrences or events, such as, for example, stroke or heart attack, that are harmful or destructive to the nerve cell via a chain of events. Non-limiting examples of noxious actions include: compressive or mechanical effects or trauma or stress factors, such as glutamate neurotoxicity, impaired blood flow to the nerves (ischemia) and with respect to the retina or optic nerves, retinitis pigmentosa and age-related macular degeneration and glaucoma.

HUMAN DOSAGE AND ADMINISTRATION

The methods of this invention are useful in treating any mammal, including humans.

According to this invention, mammals are treated with pharmaceutically effective amount of a neuroprotective agent for a period of time and at a time such that noxious provocations to the optic nerve and retina do not kill or permanently damage the nerve cells. Protective agents may be administered orally, topically to the eye or by any other appropriate means of delivery described below or known in the art.

In accordance with this invention, pharmaceutically effective amounts of a protective agent can be administered alone to treat nerve injury or to prevent nerve cell death. Alternatively a protective agent may be administered sequentially or concurrently with an antiglaucoma drug, e.g. a beta-blocker, an alpha$_2$ agonist, a muscarinic agent such as pilocarpine, a carbonic anhydrase inhibitor (CAI), or another drug useful in maintaining intraocular pressure (IOP) at normal levels or in lowering elevated IOP. The most effective mode of administration and dosage regimen of protective agent will depend on the type of disease to be treated, the severity and course of that disease, previous therapy, the patient's health status, and response to the drug and the judgment of the treating physician. Generally, the neuroprotective agent should be administered in a dose to achieve a serum or intravitreal concentration of 0.01 nM to 500 nM. Preferably the neuroprotective agent is administered prior to injury to the nerve, but can be administered after injury has occurred with lessened effect.

Conventional modes of administration and standard dosage regimens of protective agents, e.g. MK-801, can be used. Optimal dosages for co-administration of a drug, e.g. an IOP-lowering drug, with a neuroprotective agent can be determined using methods known in the art. Dosages of neuroprotective agents may be adjusted to the individual patient based on the dosage of the drug with which the agent is co-administered and the response of the patient to the treatment regimen. The protective agent may be administered to the patient at one time or over a series of treatments.

The agent may be administered locally, e.g. intravitreally by intrabulbar injection for ocular neuroprotection, or by intrathecal or epidural administration for spinal protection. Many of the agents of the invention can be administered systemically, e.g., orally, or intravenously, or by intramuscular injection. Additionally, agents for protection of the retina and optic nerve that are capable of passing through the cornea, and achieving sufficient concentration in the vitreous humor, such as AGN 191103 and brimonidine, may also be administered topically to the eye.

The composition used in these therapies may also be in a variety of forms. These include, for example, solid, semi-solid, and liquid dosage forms, such as tablets, pills, powders, preserved or non-preserved liquid solution or suspension, liposomes, suppositories, injectable and infusible solutions. The compositions also preferably include conventional pharmaceutically acceptable carriers which are known those of skill in the art.

The following non-limiting examples describe assays and measurements used in 1) determining protection of nerve cells from glutamate induced toxicity and 2) methods of determining neural protection conferred by neuroprotective agents in a nerve crush model of mechanical injury.

EXAMPLE 1

Experimental Procedure for Measuring Neural Protection in a Model of Glutamate Induced Excitotoxic Effects on Nerve Cells Low-density rat hippocampal neuronal cultures were prepared by the procedure of Goslin and Banker. Coverslips were cleaned and sterilized in porcelain racks in such a way that they did not stick to one another (Cohen cover glass staining racks, Thomas Scientific). Coverslips (13 mm) were placed in staining racks, rinsed in distilled water (four rinses, 1 min. each) to remove dust and transferred to concentrated $HNO_3$ for 36 hours. Coverslips were rinsed in distilled water (four changes over 3 hours) and sterilized with dry heat (overnight at 225° C.). The coverslips were transferred to 24-well dishes, one coverslip per well. To support the coverslips above the glia during coculturing, paraffin dots were placed on dishes, and UV irradiation (30 min.) was applied before the coverslips were introduced. One mg/mL of poly-L-lysine hydrobromide (PLL) (Sigma) (MW 30,000–70,000) was dissolved in borate buffer (0.1 M, pH 8.5), filtered, sterilized and used to cover each coverslip overnight. The PLL was removed, coverslips were rinsed in distilled water (two washes, 2 hrs. each), plating medium [Eagle's MEM with Earle's salts containing extra glucose (600 mg/L) and 10% horse serum] was added and the dishes were stored in an incubator. Astroglial cultures were prepared from the brains of neonatal rats by a method similar to that described by Levinson and Mc Carthy, except that they were plated at a lower density so that they contained predominantly type 1 astroglia. $10^5$ cells were plated in each well. Glial cultures were fed with plating medium twice a week and were used after reaching confluence, about 2 weeks after plating. One day before use, the plating medium was removed, neuronal maintenance medium (MEM containing N2 supplements) was added, and incubation continued. 3×104 of viable rat hippocampal nerves (E18 embryos) were plated on the PLL-treated coverslips kept in plating medium. After 3–4 hrs, when most of the neurons were attached, the coverslips were transferred to the dishes containing the glial cell in maintenance medium in such a way that the neuronal side was facing the glia, which support neuronal survival and development. To reduce glial proliferation, cytosine arabinoside (1-b-D-arabinofuranosylcytosine) (Calbiochem) (5×10 M final concentration) was added to the cultures 2 days after plating. At day 6 in culture, cells were treated with 1 mM glutamate or with glutamate together with either AGN-191103—0.1 nM (MW=200) or MK-801—10 nM (2–3 coverslips were used to each treatment).

After 24 hrs. of incubation, cells were stained with trypan blue. Live and dead neurons were counted from randomly selected culture fields (5 fields from each coverslip). Percentage of dead cells was calculated.

EXAMPLE 2

Procedure for Nerve Crush Injury and Measurements of Compound Action Potentials (CAP) Subsequent to Injury Part A
Metabolic Measurements Animal utilization was according to the ARVO Resolution on the use of animals in research. Male Sprague-Dawley (SPD) rats weighing 300–400 g were anesthetized with sodium pentobarbitone (intraperitoneally, 35 mg/kg). A cannula was introduced into the trachea for artificial ventilation when required. With the animal's head held in place by a head holder, a lateral canthotomy was performed under a binocular operating microscope and the conjunctiva was incised lateral to the cornea. After separation of the retractor bulbi muscles, the optic nerve was identified and a length of 3 0 3.5 mm was exposed near the eyeball by blunt dissection. The dura was left intact and care was taken not to injure the nerve. The first part of a light guide holder (see below) was inserted under the optic nerve and the nerve was gently eased into the light guide canal. The second part was then fixed in place in such a way that the light guide was located on the surface of the optic nerve 1 mm from the site at which the injury was to be administered.

Surface Fluorometry-reflectometry

Monitoring of the intramitonchodrial NADH redox state was based on fluorescence of NADH at 366 nm, resulting in the emission of blue light with a peak intensity at 450 nm, which is unlike its oxidized form, NAD+, which lacks this fluorescence. The source of the 366 nm excitation is a 100-W air-cooled mercury lamp equipped with a strong 366-nm filter (Corning 5860 (7-37) plus 9782 (4-96)). A flexible Y-shaped bundle of optic fibers (light guide) is used to transmit the light to and from the optic nerve, thus making in vivo measurements technically feasible. Excitation light is transmitted through the bundle of excitation fibers to the nerve. The light emitted from the nerve, after being transmitted through a second bundle of fibers, is split in a ratio of 90:10 for measurement of the fluorescent light (90%) at 450 nm and the reflected light (10%) at 366 run by two photomultipliers connected to a one-channel direct current fluorometer-reflectometer. In order to minimize variations among animals, standard signal calibration procedures were applied at the start of the recordings. Changes in the fluorescence and reflectance signals during the experiment are calculated relative to the calibrated signals. This type of calibration, although not absolute, has nevertheless been found to yield reliable and reproducible results from various animals and among different laboratories.

Changes in reflected light were correlated with changes in tissue absorption caused by hemodynamic effects and movements of the optic nerve secondary to alteration in arterial blood pressure and nerve volume. The fluorescence measurements are found to be adequately corrected for NADH redox state measurements by subtraction of the reflected light (366 nm) from the fluorescent light (1:1 ratio) to obtain the corrected fluorescence signal.

Metabolic Measurements

Animals which were still anesthetized were allowed to recover for 30 min. from the surgical procedures described above and were then exposed to anoxic and hyperoxic conditions. An anoxic state was achieved by having the rat breathe in an atmosphere of 100% nitrogen for 2 min., after which it was returned to air. Whenever animals did not return spontaneously to normal breathing, they were ventilated by blowing twice into the trachea. A hyperoxic state was induced by having the animal breathe 100% oxygen for 6–10 min. In order to evaluate the metabolic activity of the optic nerve, the relative changes in reflected and fluorescent light intensities in response to anoxia and to hyperoxia were measured before and after crush injury.

Experimental Protocol For Metabolic Measurements

Using calibrated cross-action forceps, a well-calibrated moderate crush injury was inflicted to the nerve between the eye and the light guide holder at a pressure corresponding to 120 g for 30 sec.

Part B

Physiological Measurements

Experimental setup for recording compound action potential (CAP): Prior to removal of optic nerves for electrophysiological measurement, the rats were deeply anesthetized with 70 mg/kg pentobarbitone. The skin was removed from the skull and the optic nerves were detached from the eyeballs. Subtotal decapitation was performed and the skull was opened with a rongeur. The cerebrum was displaced laterally, exposing the intracranial portion of the optic nerve. Dissection at the level of the chiasm enabled removal of the whole length of the nerve, which was transferred to vials containing fresh, cold Krebs solution, consisting of: NaCl (125 mM), KCl (5 mM), $KH_2PO_4$ (1.2 mM), $NaHCO_3$ (26 mM), $MgSO_4$ (0.6 mM), $CaCl_2$ (24 mM), D-glucose (11 mM), aerated with 95% $O_2$ and 5% $CO_2$. The nerves were kept in this solution, in which electrical activity remained stable for at least 3–4 h. After 1 h of recovery, nerves were immersed in Krebs solution at 37° C. Electrophysiological recording were obtained from the nerve distal to the crush lesion, since the nerves were too small to allow measurement on both sides of the crush. The nerve ends were then connected to two suction Ag-AgCl electrodes immersed in the bathing solution. The stimulating pulse was applied through the electrode at the proximal end and the action potential was recorded by the distal electrode. A Grass SD9 stimulator was used for electrical stimulation (2 V, 50 μs). The signal was transmitted to a Medelec PA63 preamplifier and thence to a Medelec MS7 electromyograph and AA7T amplifier. The solution, stimulator and amplifier had a common ground. The maximum amplitude of eight averaged CAPs was recorded and photographed with a Polaroid camera. The left nerves (uninjured) were used to measure the reference values of normal nerves and to calibrate the crush forceps.

Recording of Visual Evoked Potential (VEP) Response

Injured drug-treated rats were examined in 2 weeks after the injury for assessment of their functional recovery. In this set of experiments, the pattern of filed potentials in response to light stimulation was recorded from the primary visual cortex. The potential evoked by the light originates in the retina and is propagated along the surviving axons to reach their final target, the visual cortex. Only those axons that survived the primary and secondary degenerative processes are capable of conducting an action potential. A comparative analysis of the pattern of field potentials in treated and untreated animals will reveal the effect of the treatment on axonal survival.

Anesthetized rats (Rumpon, Ketalar) were placed in a small animal sterotaxic instrument. After exposure of the skull, two holes were drilled with a cylindrical drill bit, with the dura kept intact to minimize cortical damage. One hole, drilled above the nasal bone, was used as a reference point. The second hole was in the area OC1 with the coordinates Bregma # 8 mm, lateral # 3 mm. A gold contact pin connected to a screw was used as the electrode, which was screwed into the holes and glued by acrylic cement to the skull. The field potential was evoked by stroboscopic stimulation, with an average of 90 sweeps per minute. The flash-evoked potential was analyzed by the use of the Lab View data acquisition and management system. The field potentials were digitized and stored for off-line analysis.

Part C

Measurement of Effects of Drug Tests for Neural Protective Properties

The first set of experiments involved metabolic measurements. Each drug was injected intraperitoneally at several different concentrations. Each drug was tested in a group of 8 animals, together with 8 controls (injured animals treated with the buffer vehicle). In each case, metabolic measurements were obtained on-line before injury, 0.5 h after injury and every hour for 4–6 h thereafter. The data obtained were analyzed by ANOVA.

Measurement of Long Term Effects. Physiological Activities.

CAPS

Immediately after injury, the drug to be tested was injected into 10 animals, and 10 control animals were injected with vehicle. Two weeks later the CAPs of each nerve were recorded in vitro, using suction electrodes. The contralateral side was used as an internal control. The results indicated whether the examined drug had any potential effects on the rescue of spared axons and/or slowing of degeneration. Positive results led to efforts at determining the optimal dosage for each promising drug.

VEP Response

Electrodes were implanted in the cortex of naive SPD rats in two age- and sex-matched groups. Immediately after implantation, the VEP response was recorded from the left side while a light was flashed into the right eye, with the left eye covered. A well-controlled crush injury was then inflicted on the optic nerve and the drug was immediately administered at the previously determined optimal dosage. Control animals were handled in the same way except vehicle was administered rather than drug. The VEP response for each animal was recorded 1 day, 1 week, 2 weeks and 4 weeks after operation.

In a similar vein, it has been demonstrated that nerve cell damage occurs in models of spinal ischemia, and suggested that induced spinal hypothermia has neuroprotective effect. Marsala, M, Gulik, J., Ishikawa, T. and Yaksh, T. L., *Journal of Neuroscience Methods* 74, pp 97–106 (1997). The mechanism of nerve cell death following ischemia is believed to be by mechanisms similar to those found to be effectively treated by the administration of compounds of the present invention in nerves such as the optic nerve and retina. Hypoxic neuronal depolarization and glutamate toxicity are cited in the study by Marsala, Galik, et al (supra).

Recent studies have shown that adrenergic $\alpha_{2A}$ receptors are the predominant $\alpha_2$ subtype localized in the human spinal cord. It has been suggested previously that $\alpha_{2A}$ agonists may be useful in analgesia or sedation by binding to and activation of $\alpha_{2A}$ receptors in the spine. See for example, Lawhead, R. G., Blaxall, H. S., and Bylund, D. B. *Anesthesiology*, 77(5) 983–91 (1992). It is newly found that these agonists will impart neuroprotection to the cells of the spine. Administration of an effective amount of the compounds of the invention for neuroprotection in the spine may be made intrathecally, epidurally or systemically, such as orally or by injection, as discussed above under "Dosage and Administration". Such administration to the spinal cord will protect spinal nerve cells from noxious provocations such as ischemia and trauma.

Animal models of spinal ischemia; methods of inducing such ischemia, methods for measuring amounts of endogenous compounds released during and after ischemia using intrathecal dialysis and histological studies of the nerve tissues and behavioral neurologic function after ischemic events are provided in the following papers: Marsala, M, Malmberg, A. B., and Yaksh, T. L., *J. Neuroscience Methods,* 62, pp. 43–53 (1995); Taira, Y., Marsala, M., *Stroke,* 27 (10), pp. 1850–58 (1996); Marsala, M., Vanicky, I., Yaksh, T. L., *Stroke,* 25 (10), pp. 2038–46 (1994).

Using the combination of these references an experiment is used to test the effectiveness of the compounds of the invention. The compounds are administered to a test animal, for example a rat, followed by induction of spinal ischemia and then reperfusion, or calibrated nerve crush damage. Measurement of release of glutamate, and other endogenous compounds is made by use of intrathecal dialysis. Also the study of neurologic behavior modifications, such as induction of allodynia and loss of motor abilities is made to demonstrate the usefulness of the compounds for spinal neuroprotecetion against a control group of animals that are not treated with neuroprotective compounds.

While this invention has been described with respect to various specific examples and embodiments, it is to be understood that the invention is not limited thereby and should only be construed by interpretation of the scope of the appended claims.

What is claimed is:

1. A method of protecting the optic nerve and retina of a mammal comprising administering to said mammal suffering from or at risk of suffering a noxious action on said nerve cells an effective amount of a compound of formula I to inhibit or prevent nerve cell injury or death

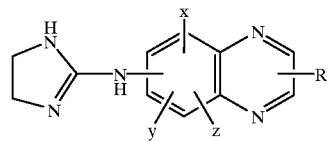

formula I wherein the 2-imidazolin-2-ylamino group is in either the 5- or 6-position of the quinoxaline nucleus; x, y and z are in any of the remaining 5-, 6-, 7- or 8-positions and are selected from hydrogen, halogen, lower alkyl, lower alkoxy or trifluoromethyl; and R is an optional substituent in either the 2- or 3-position of the quinoxaline nucleus and may be hydrogen, lower alkyl or lower alkoxy, or pharmaceutically acceptable salts thereof and mixtures thereof, wherein said noxious action is selected from the group consisting of glaucomatous optic neuropathy, atrophy associated with dry ARMD, laser light directed into the eye in a procedure for treatment of wet ARMD, ischemia secondary to glaucoma and photoreceptor cell damage associated with retinitis pigmentosa.

2. The method of claim 1 wherein the noxious action is glaucomatous optic neuropathy.

3. The method of claim 1 wherein the noxious action is atrophy associated with dry ARMD.

4. The method of claim 1 wherein the noxious action is laser light directed into the eye in a procedure for treatment of wet ARMD.

5. The method of claim 1 wherein the noxious action is ischemia secondary to glaucoma.

6. The method of claim 1 wherein the noxious action is photoreceptor cell damage associated with retinitis pigmentosa.

* * * * *